United States Patent
Gardel et al.

(10) Patent No.: US 8,529,918 B2
(45) Date of Patent: *Sep. 10, 2013

(54) WATER-IN OIL EMULSION FOUNDATION COMPRISING A POLYOL

(75) Inventors: Nadia Gardel, Bourg la Reine (FR); Véronique Barrois, Paris (FR); Sandrine Champenois, Gennevilliers (FR)

(73) Assignee: L'Oreal, Paris (FR)

( * ) Notice: Subject to any disclaimer, the term of this patent is extended or adjusted under 35 U.S.C. 154(b) by 1764 days.

This patent is subject to a terminal disclaimer.

(21) Appl. No.: 10/784,909

(22) Filed: Feb. 24, 2004

(65) Prior Publication Data

US 2006/0024251 A1 Feb. 2, 2006

Related U.S. Application Data

(60) Provisional application No. 60/506,774, filed on Sep. 30, 2003.

(30) Foreign Application Priority Data

Mar. 22, 2003 (FR) ...................................... 03 06150

(51) Int. Cl.
*A61K 8/04* (2006.01)

(52) U.S. Cl.
USPC .............. 424/401; 424/63; 514/844; 514/845

(58) Field of Classification Search
USPC .............................. 424/63, 401; 514/844, 845
See application file for complete search history.

(56) References Cited

U.S. PATENT DOCUMENTS

| | | | |
|---|---|---|---|
| 4,552,753 A * | 11/1985 | Elm et al. | 424/66 |
| 4,735,742 A * | 4/1988 | Ansmann | 516/67 |
| 5,196,187 A * | 3/1993 | Nicoll et al. | 424/70.12 |
| 5,340,582 A | 8/1994 | Sugasawa et al. | |
| 5,830,449 A | 11/1998 | Afriat et al. | |
| 5,843,417 A * | 12/1998 | Hanna et al. | 424/70.7 |
| 5,902,592 A * | 5/1999 | Bara et al. | 424/401 |
| 6,254,877 B1 | 7/2001 | de la Poterie et al. | |
| 6,326,013 B1 | 12/2001 | Lemann et al. | |
| 6,344,204 B1 | 2/2002 | Lorant | |
| 6,440,430 B1 | 8/2002 | Bara et al. | |
| 2004/0009131 A1 | 1/2004 | Simonnet et al. | |
| 2005/0008592 A1 * | 1/2005 | Gardel et al. | 424/63 |

FOREIGN PATENT DOCUMENTS

| | | |
|---|---|---|
| EP | 1 086 683 | 10/2002 |
| EP | 1 112 744 | 3/2005 |
| FR | 2 737 115 | 1/1997 |
| FR | 2 776 514 | 10/1999 |
| FR | 2 783 415 | 3/2000 |
| FR | 2 789 313 | 8/2000 |
| FR | 2 839 259 | 11/2003 |
| JP | 02-062816 | 3/1990 |
| JP | A-H05-329359 | 12/1993 |
| JP | H07-138144 | 5/1995 |
| JP | H09-40544 | 2/1997 |
| JP | A-H09-136821 | 5/1997 |
| JP | H09-136821 | 5/1997 |
| JP | T-H11-504326 | 4/1999 |
| JP | 2000-119124 | 4/2000 |
| JP | 2000-229838 | 8/2000 |
| JP | 2001-240548 | 9/2001 |
| JP | 2002-020234 A | 1/2002 |
| JP | 2002-265333 A | 9/2002 |
| JP | 2002-265620 A | 9/2002 |
| JP | 2002-308734 | 10/2002 |
| JP | 2003-012488 | 1/2003 |
| JP | 2003-321345 | 11/2003 |
| WO | WO 96/33689 | 10/1996 |

OTHER PUBLICATIONS

Derwent Abstract of JP 2003012488.
Derwent Abstract of JP 5329359.
Derwent Abstract of JP 9136821.
Derwent Abstract of JP 11504326.
JP H07-138144 Patent Abstracts of Japan translation.
JP H09-136821 Patent Abstracts of Japan translation.

* cited by examiner

*Primary Examiner* — Ali Soroush
(74) *Attorney, Agent, or Firm* — Oblon, Spivak, McClelland Maier & Neustadt, L.L.P.

(57) ABSTRACT

The invention relates to a fluid foundation in the form of water-in-oil emulsion comprising an oil and an aqueous phase comprising a polyol, and optionally polymethyl methacrylate particles, the water+polyol/oil weight ratio being greater than or equal to 0.8. The foundation slides well on the skin and has a sensation of lightness when applied.

78 Claims, No Drawings

WATER-IN OIL EMULSION FOUNDATION COMPRISING A POLYOL

This application claims benefit of U.S. Provisional Application No. 60/506,774, filed Sep. 30, 2003, the contents of which are incorporated herein by reference. This application also claims benefit of priority under 35 U.S.C. §119 to French Patent Application No. 03/06150, filed March 22, 2003, the contents of which are also incorporated by reference.

The present invention relates to a fluid foundation cosmetic composition in the form of a water-in-oil emulsion comprising an oil and a polyol. The invention also relates to a process for making up the skin comprising the application of the foundation to the skin.

The foundation composition is a composition for making up human skin. The composition according to the invention may be a foundation to be applied to the face or the neck, a concealer product, a tinted cream or a body makeup composition.

The foundation compositions are commonly employed to give an attractive color to the skin and especially to the face, but also to camouflage skin imperfections such as redness and marks.

These compositions have varied textures ranging from fluid to solid and generally contain oils and pulverulent dyestuffs. One of the difficulties encountered by users is that of uniformly spreading the foundation over the entire surface of the face so as to uniformly distribute the product. Compositions with thick or solid textures are difficult to spread on account of their high viscosities. Compositions with fluid textures are not always suitable for obtaining a uniform makeup, since they do not leave visible marks on the skin, especially on account of their poor spreading over the entire surface of the face to be made up.

The aim of the present invention is to provide a foundation composition that has good sliding properties when applied to the skin, allowing a uniform and/or mark-free makeup result to be obtained on the skin.

The inventors have discovered that such a foundation can be obtained by using oils, polyols and water in particular contents.

More specifically, one subject of the invention is a fluid foundation composition in the form of a water-in-oil emulsion comprising at least one oil, an aqueous phase containing water and at least 6% by weight, relative to the total weight of the composition, of water-miscible polyol, and at least 8% by weight of dyestuff, the water, the polyol and the oil being present in a content such that the water+polyol/oil(s) weight ratio is greater than or equal to 0.8.

A subject of the invention is also a fluid foundation composition in the form of a water-in-oil emulsion comprising at least one oil, an aqueous phase containing water and at least 5% by weight, relative to the total weight of the composition, of water-miscible polyol, and polymethyl methacrylate particles, the polyol and the oil being present in a content such that the water+polyol/oil(s) weight ratio is greater than or equal to 0.8.

A subject of the invention is also a fluid foundation composition in the form of a water-in-oil emulsion comprising at least one oil, and an aqueous phase containing water and at least two water-miscible polyols, the polyols being present in a total content of greater than or equal to 5% by weight, relative to the total weight of the composition, the polyols and the oil being present in a content such that the water+polyols/oil(s) weight ratio is greater than or equal to 0.8.

A subject of the invention is also a fluid foundation composition in the form of a water-in-oil emulsion comprising at least one oil, an aqueous phase containing water and at least two water-miscible polyols, and polymethyl methacrylate particles, the water being the predominant compound of the emulsion, the composition having a viscosity ranging from 0.25 Pa·s to 0.6 Pa·s.

A subject of the invention is also a nontherapeutic cosmetic process for making up the skin, comprising the application to the skin of a composition as defined above.

A subject of the invention is also the use of a composition as defined above to obtain a uniform and/or mark-free makeup result on the skin.

The composition according to the invention has a light fluid texture and good sliding properties when applied to the skin. The foundation can thus be spread easily over the entire surface of the skin to be made up and is uniformly distributed over the face. In particular, it does not form a thick layer on the skin and the user does not have a sensation of heaviness of the makeup thus applied. This light and fluid texture is suitable for the formulation of a high content of particles such as pigments and fillers without having a harmful effect when the makeup is applied and makes it possible especially to obtain a foundation with good coverage properties (masking of skin imperfections). In addition, the deposition of foundation on the skin can be easily modulated by the user, who can thus deposit, depending on the areas of the skin, a thicker or thinner coat according to the intensity of the skin defects to be camouflaged; this deposition takes place without creating a thickness effect. The user has a sensation of a fluid and fondant product when he or she applies the composition to the skin.

The term "fluid composition" means a composition capable of flowing under its own weight in less than 5 minutes, at room temperature (25° C.).

The oil present in the composition according to the invention may be chosen from hydrocarbon-based oils, silicone oils and fluoro oils, and mixtures thereof. The oils mentioned above may be volatile oils or nonvolatile oils, and mixtures thereof.

The oil advantageously comprises at least one volatile oil.

The term "hydrocarbon-based oil" means an oil formed essentially, or even consisting, of carbon and hydrogen atoms, and possibly oxygen and nitrogen atoms, and containing no silicone or fluorine atoms; it may contain ester, ether, amine or amide groups.

The term "silicone oil" means an oil containing at least one silicon atom and especially containing Si—O groups.

The term "fluoro oil" means an oil containing at least one fluorine atom.

The term "volatile oil" means an oil (or nonaqueous medium) capable of evaporating on contact with the skin in less than one hour, at room temperature and atmospheric pressure. The volatile oil is a volatile cosmetic oil, which is liquid at room temperature, especially having a nonzero vapor pressure, at room temperature and atmospheric pressure, in particular having a vapor pressure ranging from 0.13 Pa to 40 000 Pa ($10^{-3}$ to 300 mm Hg), and preferably ranging from 1.3 Pa to 13 000 Pa (0.01 to 100 mm Hg), and preferably ranging from 1.3 Pa to 1300 Pa (0.01 to 10 mm Hg).

In addition, the volatile oil generally has a boiling point, measured at atmospheric pressure, ranging from 150° C. to 260° C. and preferably ranging from 170° C. to 250° C.

The composition according to the invention may comprise a volatile hydrocarbon-based oil chosen especially from hydrocarbon-based oils with a flash point ranging from 40° C. to 102° C., preferably ranging from 40° C. to 55° C. and preferentially ranging from 40° C. to 50° C.

Volatile hydrocarbon-based oils that may be mentioned include volatile hydrocarbon-based oils containing from 8 to 16 carbon atoms and mixtures thereof, and especially branched $C_8$-$C_{16}$ alkanes, for instance $C_8$-$C_{16}$ isoalkanes (also known as isoparaffins), isododecane, isodecane, isohexadecane and, for example, the oils sold under the trade names Isopars or Permetyls, branched $C_8$-$C_{16}$ esters, for instance isohexyl neopentanoate, and mixtures thereof. Preferably, the volatile hydrocarbon-based oil is chosen from volatile hydrocarbon-based oils containing from 8 to 16 carbon atoms and mixtures thereof, in particular from isododecane, isodecane and isohexadecane, and is especially isododecane.

The volatile hydrocarbon-based oil may be present in a content ranging from 5% to 35% by weight, preferably ranging from 5% to 25% by weight, preferentially ranging from 5% to 20% by weight and more preferentially ranging from 8% to 15% by weight, relative to the total weight of the composition.

The composition according to the invention may comprise a volatile silicone oil chosen especially from silicone oils with a flash point ranging from 40° C. to 102° C., preferably with a flash point of greater than 55° C. and less than or equal to 95° C., and preferentially ranging from 65° C. to 95° C.

Volatile silicone oils that may be mentioned include linear or cyclic silicone oils containing from 2 to 7 silicon atoms, these silicones optionally comprising alkyl or alkoxy groups containing from 1 to 10 carbon atoms. Examples of volatile silicone oils that may especially be mentioned include octamethylcyclotetrasiloxane, decamethylcyclopentasiloxane, dodecamethylcyclohexasiloxane, heptamethyl-hexyltrisiloxane, heptamethyloctyltrisiloxane, hexamethyldisiloxane, octamethyl-trisiloxane, decamethyltetrasiloxane and dodecamethylpentasiloxane, and mixtures thereof.

The volatile silicone oil may be present in a content ranging from 5% to 35% by weight, preferably ranging from 10% to 30% by weight and preferentially ranging from 15% to 25% by weight, relative to the total weight of the composition. The volatile fluoro oil generally does not have a flash point.

Volatile fluoro oils that may be mentioned include nonafluoroethoxybutane, nonafluoromethoxybutane, decafluoropentane, tetradecafluorohexane and dodecafluoropentane, and mixtures thereof.

Advantageously, the composition according to the invention may comprise at least one volatile hydrocarbon-based oil and at least one volatile silicone oil.

The volatile oil, chosen especially from volatile hydrocarbon-based oils, the volatile silicone oils, and mixtures thereof, may be present in a total content ranging from 10% to 50% by weight, preferably ranging from 15% to 45% by weight, preferentially ranging from 20% to 40% by weight, preferentially ranging from 25% to 40% by weight, more preferentially ranging from 30% to 40% by weight and even more preferentially ranging from 30% to 36% by weight, relative to the total weight of the composition.

According to one preferred embodiment of the invention, the composition may comprise:
a first volatile hydrocarbon-based oil,
a second volatile silicone oil with a flash point of greater than 55° C. and less than or equal to 80° C., preferably ranging from 65° C. to 80° C. and better still ranging from 67° C. to 85° C.,
a third volatile silicone oil with a flash point of greater than 80° C., preferably greater than or equal to 80° C. and less than or equal to 95° C., and better still ranging from 87° C. to 95° C.

In this embodiment:
the first volatile hydrocarbon-based oil may be an isoparaffin and in particular isododecane;
the second volatile silicone oil may be decamethylcyclopentasiloxane or decamethyltetrasiloxane, and preferably decamethylcyclopentasiloxane;
the third volatile silicone oil may be dodecamethylcyclohexasiloxane.

Advantageously, the first volatile hydrocarbon-based oil, and especially isododecane, may be present in a content ranging from 6% to 25% by weight, preferably ranging from 10% to 20% by weight and preferentially ranging from 10% to 15% by weight, relative to the total weight of the composition.

Advantageously, the second volatile silicone oil, and especially decamethylcyclopentasiloxane, may be present in a content ranging from 0.1% to 35% by weight, preferably ranging from 5% to 20% by weight and preferentially ranging from 8% to 16% by weight, relative to the total weight of the composition.

Advantageously, the third volatile silicone oil, and especially dodecamethylcyclohexasiloxane, may be present in a content ranging from 0.1% to 35% by weight, preferably ranging from 2% to 20% by weight and preferentially ranging from 4% to 15% by weight, relative to the total weight of the composition.

According to one particularly preferred embodiment of the invention, the composition comprises a mixture of isododecane, decamethylcyclopentasiloxane and dodecamethylcyclohexasiloxane. In particular, in this mixture, the content, expressed on a weight basis relative to the total weight of the composition, is such that: isododecane content>decamethylcyclopentasiloxane content>dodecamethylcyclohexasiloxane content.

Advantageously, the composition comprises isododecane present as volatile oil in predominant weight amount, which means that the weight content of isododecane, relative to the total weight of the composition, is greater than the weight content of any other volatile oil that may be present in the composition.

According to one embodiment of the composition according to the invention, the composition comprises decamethylcyclopentasiloxane in predominant (weight) amount relative to the weight content of any other volatile silicone oil that may be present in the composition.

The composition according to the invention may also comprise at least one nonvolatile oil.

The nonvolatile oil may be present in a content ranging from 0.1% to 12% by weight and preferably ranging from 1% to 5% by weight relative to the total weight of the composition.

The composition according to the invention may advantageously comprise from 30% to 45% by weight and preferably from 30% to 40% by weight of oils relative to the total weight of the composition.

The nonvolatile oil may be chosen from oils of mineral, animal, plant or synthetic origin, carbon-based oils, hydrocarbon-based oils and/or silicone oils, and mixtures thereof, provided that they are compatible with the intended use.

Mention may be made of nonvolatile hydrocarbon-based oils such as liquid paraffin or liquid petroleum jelly, isoeicosane, mink oil, turtle oil, soybean oil, perhydrosqualene, sweet almond oil, beauty-leaf oil, palm oil, grape seed oil, sesame seed oil, maize oil, arara oil, rapeseed oil, sunflower oil, cotton seed oil, apricot oil, castor oil, avocado oil, jojoba oil, olive oil or cereal germ oil; lanolic acid, oleic acid, lauric acid or stearic acid esters; fatty esters, such as isopropyl myristate, isopropyl palmitate, butyl stearate, hexyl laurate, diisopropyl adipate, isononyl isononanoate, isostearyl neopentanoate, 2-ethylhexyl palmitate, 2-hexyldecyl laurate, 2-octyldecyl palmitate, 2-octyldodedcyl myristate or lactate, 2-diethylhexyl succinate, diisostearyl malate, and glyceryl or diglyceryl triisostearate; behenic acid, oleic acid, linoleic acid or linolenic acid; higher fatty alcohols such as cetanol, stearyl alcohol, oleyl alcohol, linoleyl alcohol, linolenyl alcohol, isostearyl alcohol or octyldodecanol.

Nonvolatile silicone oils that may be mentioned include polydimethylsiloxanes (PDMS), which are optionally phenylated, such as phenyltrimethicones, or optionally substituted with aliphatic and/or aromatic groups or with functional groups such as hydroxyl, thiol and/or amine groups; polysiloxanes modified with fatty acids, fatty alcohols or polyoxyalkylenes, and mixtures thereof.

The composition according to the invention may also comprise an oil thickener. The thickener may be chosen from:

organomodified clays, which are clays treated with compounds chosen especially from quaternary amines and tertiary amines. Organomodified clays that may be mentioned include organomodified bentonites such as those sold under the name "Bentone 34" by the company Elementis, and organomodified hectorites such as those sold under the names "Bentone 27", "Bentone 38" and "Bentone 38 V" by the company Elementis;

hydrophobic fumed silica, which is a fumed silica that has been chemically surface-modified by chemical reaction generating a reduction in the number of silanol groups. The silanol groups may especially be substituted with hydrophobic groups.

The hydrophobic groups may be:

trimethylsiloxyl groups, which are obtained especially by treating fumed silica in the presence of hexaymethyidisilazane. Silicas thus treated are known as "Silica silylate" according to the CTFA ($6^{th}$ edition, 1995). They are sold, for example, under the references "AEROSIL R812®" by the company Degussa and "CAB-O-SIL TS-530®" by the company Cabot.

dimethylsilyloxyl or polydimethylsiloxane groups, which are obtained especially by treating fumed silica in the presence of polydimethylsiloxane or dimethyldichlorosilane. Silicas thus treated are known as "Silica dimethyl silylate" according to the CTFA (6th edition, 1995). They are sold, for example, under the references "AEROSIL R972®" and "AEROSIL R974®" by the company Degussa, and "CAB-O-SIL TS-6100", and "CAB-O-SIL TS-720®" by the company Cabot.

The fumed silica preferably has a particle size that may be nanometric or micrometric, for example ranging from about 5 to 200 nm.

The oil thickener may be present in a content ranging from 0.1% to 5% by weight and better still from 0.4% to 3% by weight relative to the total weight of the composition.

The aqueous phase comprises water. The water may be a floral water such as cornflower water and/or a mineral water such as Vittel, Lucas or La Roche Posay and/or a spring water.

According to one preferred embodiment of the invention, water is the predominant compound by weight in the composition (water is the ingredient present in largest weight amount in the composition).

The water may be present in a content ranging from 15% to 35% by weight, preferably ranging from 20% to 30% by weight and preferentially ranging from 22% to 28% by weight relative to the total weight of the composition.

The aqueous phase comprises at least one polyol that is water-miscible, especially at room temperature (25° C.). Water-miscible polyols that may be mentioned include polyols especially containing from 3 to 20 carbon atoms, preferably containing from 3 to 10 carbon atoms and preferentially containing from 3 to 6 carbon atoms, such as glycerol, propylene glycol, butylene glycol, pentylene glycol, hexylene glycol, dipropylene glycol or diethylene glycol, and the mixtures thereof.

The polyol(s) may be present in a content ranging from 5% to 20% by weight, especially ranging from 5% to 17% by weight, preferably of at least 6% by weight, especially ranging from 6% to 20% by weight, preferentially ranging from 6% to 17% by weight and more preferentially ranging from 8% to 12% by weight, relative to the total weight of the composition.

Advantageously, the composition may comprises at least two water-miscible polyols, especially a water-miscible polyol containing 3 carbon atoms and a water-miscible polyol containing more than 3 carbon atoms, especially containing from 4 to 20 carbon atoms, preferably containing from 4 to 10 carbon atoms and preferentially containing from 4 to 6 carbon atoms, and which may be chosen from the polyols mentioned above. According to one particular embodiment of the invention, the polyol containing 3 carbon atoms is present in predominant weight amount in the mixture of polyols present in the composition (which means that the weight content of polyol containing 3 carbon atoms is greater than the total content of water-miscible polyol containing more than 3 carbon atoms).

The polyol containing 3 carbon atoms may be present in a content ranging from 3% to 15% by weight, preferably ranging from 3% to 10% by weight and preferentially ranging from 5% to 8% by weight, relative to the total weight of the composition.

The water-miscible polyol containing more than 3 carbon atoms may be present in a content ranging from 1% to 7% by weight, preferably ranging from 1% to 5% by weight and preferentially ranging from 2% to 4% by weight, relative to the total weight of the composition.

The aqueous phase may also comprise stabilizers, for example sodium chloride, magnesium dichloride and magnesium sulfate.

The aqueous phase may also comprise any water-soluble or water-dispersible compound that is compatible with an aqueous phase, such as gelling agents, film-forming polymers, thickeners and surfactants, and mixtures thereof.

Preferably, the aqueous phase may be present in the emulsion according to the invention in a content ranging from 20% to 50% by weight, preferably ranging from 25% to 40% by weight and preferentially ranging from 30% to 40% by weight, relative to the total weight of the composition.

Advantageously, the composition according to the invention comprises water, at least one polyol and at least one oil in a content such that the water+polyol(s)/oil(s) weight ratio is greater than or equal to 0.8 (especially ranging from 0.8 to 1.2), preferably greater than or equal to 0.85 (especially ranging from 0.85 to 1.2), preferentially greater than or equal to 0.9 (especially ranging from 0.9 to 1.2), and more preferentially greater than or equal to 0.94 (especially ranging from 0.94 to 1.2).

The composition according to the invention advantageously comprises an emulsifier that is capable in particular of forming a water-in-oil emulsion.

The emulsifier may especially be a $C_8$-$C_{22}$ alkyl dimethicone copolyol, i.e. an oxypropylenated and/or oxyethylenated polymethyl ($C_8$-$C_{22}$)alkyl dimethylmethylsiloxane.

The $C_8$-$C_{22}$ alkyl dimethicone copolyol is advantageously a compound of formula (I) below:

$$(CH_3)_3Si-O-\left[\begin{array}{c}CH_3\\|\\Si-O\\|\\(CH_2)_p\\|\\CH_3\end{array}\right]_o-\left[\begin{array}{c}CH_3\\|\\Si-O\\|\\(CH_2)_q\\|\\O\\|\\PE\end{array}\right]_m-\left[\begin{array}{c}CH_3\\|\\Si-O\\|\\CH_3\end{array}\right]_n-Si(CH_3)_3 \quad (I)$$

in which:
PE represents $(-C_2H_4O)_x-(C_3H_6O)_y-R$, R being chosen from a hydrogen atom and an alkyl radical of 1 to 4 carbon atoms, x ranging from 0 to 100 and y ranging from 0 to 80, x plus y not simultaneously being 0
m ranging from 1 to 40
n ranging from 10 to 200
o ranging from 1 to 100
p ranging from 7 to 21
q ranging 0 to 4
and preferably:
R=H
m=1 to 10
n=10 to 100
o=1 to 30
p=15
q=3

$C_6$-$C_{22}$ alkyl dimethicone copolyols that may be mentioned included cetyl dimethicone copolyol, for instance the product sold under the name Abil EM-90 by the company Goldschmidt.

The $C_8$-$C_{22}$ alkyl dimethicone copolyol may be present in the composition according to the invention in a content ranging from 0.5% to 2% by weight, especially ranging from 0.6% to 2% by weight, better still ranging from 0.7% to 2% by weight, preferably ranging from 0.5% to 1.5% by weight, especially ranging from 0.6% to 1.5% by weight and better still ranging from 0.7% to 1.5% by weight, relative to the total weight of the composition.

The composition may also comprise as emulsifier a dimethicone copolyol, i.e. an oxypropylenated and/or oxyethylenated polydimethylmethylsiloxane. It does not contain any long-chain alkyl groups of more than 8 carbon atoms, and especially of $C_8$-$C_{22}$.

Dimethicone copolyols that may be used include those corresponding to formula (II) below:

$$R_1-\underset{\underset{CH_3}{|}}{\overset{\overset{CH_3}{|}}{Si}}O-\left[\underset{\underset{CH_3}{|}}{\overset{\overset{CH_3}{|}}{Si}}O\right]_A-\left[\underset{\underset{R_2}{|}}{\overset{\overset{CH_3}{|}}{Si}}O\right]_B-\underset{\underset{CH_3}{|}}{\overset{\overset{CH_3}{|}}{Si}}-R_3 \quad (II)$$

in which:
$R_1$, $R_2$ and $R_3$, independently of each other, represent a $C_1$-$C_6$ alkyl radical or a radical $-(CH_2)_x-(OCH_2CH_2)_y-(OCH_2CH_2CH_2)_z-OR_4$, at least one radical $R_1$, $R_2$ or $R_3$ not being an alkyl radical; $R_4$ being a hydrogen, a $C_1$-$C_3$ alkyl radical or a $C_2$-$C_4$ acyl radical;
A is an integer ranging from 0 to 200;
B is an integer ranging from 0 to 50; with the condition that A and B are not simultaneously equal to 0;
x is an integer ranging from 1 to 6;
y is an integer ranging from 1 to 30
z is an integer ranging from 0 to 5.

According to one preferred embodiment of the invention, in the compound of formula (II), $R_1$=$R_3$=methyl radical, x is an integer ranging from 2 to 6 and y is an integer ranging from 4 to 30. $R_4$ is in particular a hydrogen.

Examples of compounds of formula (II) that may be mentioned included the compounds of formula (III):

$$(CH_3)_3SiO-[(CH_3)_2SiO]_A-(CH_3SiO)_B-Si(CH_3)_3 \quad (III)$$
$$\qquad\qquad\qquad\qquad\qquad\qquad |$$
$$\qquad\qquad\qquad\qquad\qquad (CH_2)_2-(OCH_2CH_2)_y-OH$$

in which A is an integer ranging from 20 to 105, B is an integer ranging from 2 to 10 and y is an integer ranging from 10 to 20.

Examples of silicone compounds of formula (II) that may also be mentioned include the compounds of formula (IV):

$$HO-(CH_2CH_2O)_y-(CH_2)_3-[(CH_3)_2SiO]_{A'}-[(CH_3)_2Si]-(CH_2)_3-(OCH_2CH_2)_y-OH \quad (IV)$$

in which A' and y are integers ranging from 10 to 20.

Dimethicone copolyols that may be used include those sold under the names DC 5329, DC 7439-146, DC 2-5695 and Q4-3667 by the company Dow Corning; KF-6013, KF-6015, KF-6016 and KF-6017 by the company Shin-Etsu.
The compounds DC 5329, DC 7439-146 and DC 2-5695 are compounds of formula (III) in which, respectively, A is 22, B is 2 and y is 12; A is 103, B is 10 and y is 12; A is 27, B is 3 and y is 12.

The dimethicone copolyol may be present in the composition according to the invention in a content ranging from 2% to 10% by weight, preferably ranging from 2% to 8% by weight and preferentially ranging from 2% to 7% by weight, relative to the total weight of the composition.

The foundation composition according to the invention advantageously comprises one or more dyestuffs, in particular one or more pulverulent dyestuff(s) chosen especially from pigments and nacres, and mixtures thereof.

The term "pigments" should be understood as meaning white or colored, mineral or organic particles of any form, which are insoluble in the physiological medium, and which are intended to color the composition.

The term "nacres" should be understood as meaning iridescent particles of any form, produced especially by certain mollusks in their shell, or alternatively synthesized.

The pigments may be white or colored, and mineral and/or organic. Among the mineral pigments that may be mentioned are titanium dioxide, optionally surface-treated, zirconium oxide or cerium oxide, and also zinc oxide, iron oxide (black, yellow or red) or chromium oxide, manganese violet, ultramarine blue, chromium hydrate, Prussian blue, ferric blue, bismuth oxychloride and metal powders, for instance aluminum powder or copper powder.

Iron oxide or titanium dioxide pigments are preferably used.
Among the organic pigments that may be mentioned are carbon black, pigments of D & C type and lakes, especially lakes based on cochineal carmine or on barium, strontium, calcium or aluminum.

The nacres may be chosen from white nacreous pigments such as mica coated with titanium or with bismuth oxychloride, colored nacreous pigments such as titanium mica coated with iron oxides, titanium mica coated especially with ferric blue or with chromium oxide, titanium mica coated with an organic pigment of the abovementioned type, and also nacreous pigments based on bismuth oxychloride.

Advantageously, the dyestuffs may be hydrophobic-coated: these dyestuffs are surface-treated with a hydrophobic agent to make them compatible with the fatty phase of the emulsion, especially such that they have good wettability with the oils of the fatty phase. Thus, these treated dyestuffs are well dispersed in the fatty phase.

The hydrophobic treatment agent may be chosen from silicones, for instance methicones, dimethicones or perfluoroalkylsilanes; fatty acids, for instance, stearic acid; metal soaps, for instance aluminum dimyristate, the aluminum salt of hydrogenated tallow glutamate, perfluoroalkyl phosphates, perfluoroalkylsilanes, perfluoroalkylsilazanes, polyhexafluoropropylene oxides, polyorganosiloxanes comprising perfluoroalkyl perfluoropolyether groups, and amino acids; N-acylamino acids or salts thereof; lecithin, isopropyl trisostearyl titanate, and mixtures thereof.

The N-acylamino acids may comprise an acyl group containing from 8 to 22 carbon atoms, for instance a 2-ethylhexanoyl, caproyl, lauroyl, myristoyl, palmitoyl, stearoyle or cocoyl group. The salts of these compounds may be the aluminum, magnesium, calcium, zirconium, zinc, sodium or potassium salts. The amino acid may be, for example, lysine, glutamic acid or alanine.

The term "alkyl" mentioned in the compounds mentioned above especially denotes an alkyl group containing from 1 to 30 carbon atoms and preferably containing from 5 to 16 carbon atoms.

Hydrophobic-treated pigments or nacres are described especially in patent application EP-A-1 086 683.

The pulverulent dyestuffs, optionally with a hydrophobic coating, may be present in a content ranging from 0.5% to 20% by weight, preferably in a content at least equal to 5% by weight, especially ranging from 5% to 20% by weight, preferentially at least equal to 8% by weight, especially ranging from 8% to 20% by weight and in particular ranging from 8% to 15% by weight, relative to the total weight of the composition.

Advantageously, the composition according to the invention may comprise polymethyl methacrylate particles.

The polymethyl methacrylate powders are generally in the form of hollow or solid white spherical particles generally with a micrometer-scale number-average size, in particular ranging from 5 to 20 microns and generally ranging from 7 to 15 microns. The expression "number-average size" denotes the size given by the statistical particle size distribution to half of the population, referred to as D50.

It is also possible to characterize these polymethyl methacrylate particles by their density, which can vary especially as a function of the size of the spherical cavity of said particles.

In the context of the present invention, this density is assessed according to the following protocol, referred as the packed density: m=40 g of powder is poured into a measuring cylinder; the measuring cylinder is then placed on a Stav 2003 machine from Stampf Volumeter; the measuring cylinder is then subjected to 1500 packing motions; the final volume Vf of packed powder is then measured directly on the measuring cylinder. The packed density is determined by the ratio m/Vf, in this instance 40/Vf (Vf being expressed in cm$^3$ and m in g).

In particular, the density of the polymethyl methacrylate particles that may be used according to the invention may range from 0.3 to 0.95, especially from 0.45 to 0.80 and more particularly from 0.5 to 0.75.

As nonlimiting illustrations of the polymethyl methacrylates that are suitable for the invention, mention may be made especially of the polymethyl methacrylate particles sold by the company Wackherr under the name Covabead LH 85 and those sold by the company Nihon Junyaku under the name Jurymer MB1.

The polymethyl methacrylate particles may be present in a content ranging from 1% to 10% by weight, preferably ranging from 1% to 8% by weight, preferentially ranging from 1% to 6% by weight and more preferentially ranging from 2% to 6% by weight, relative to the total weight of the composition.

Advantageously, the composition according to the invention may comprise pulverulent dyestuffs (especially pigments and nacres) and polymethyl methacrylate (PMMA) particles in contents such that the pulverulent dyestuff/PMMA weight ratio ranges from 2.5 to 3.5 and preferably ranges from 3 to 3.5.

The composition according to the invention may comprise an additional filler, other than the polymethyl methacrylate particles. The term "fillers" should be understood as meaning colorless or white, mineral or synthetic, lamellar or nonlamellar particles.

The additional fillers may be present in the composition in a content ranging from 0.1% to 5% by weight and preferably 0.1% to 3% by weight, relative to the total weight of the composition. Mention may be made especially of talc, mica, silica, kaolin, starch, boron nitride, calcium carbonate, magnesium carbonate, magnesium hydrocarbonate, microcrystalline cellulose, polyester powders, polyamide powders such as those sold under the trade name "Nylon", polytetrafluoroethylene ("Teflon") and silicone powders.

Advantageously, the composition according to the invention comprises a total content of solid particles, especially of pulverulent dyestuff (including pigments and nacres), polymethyl methacrylate and additional fillers, of less than or equal to 20% by weight (especially ranging from 1% to 20% by weight), preferably ranging from 5% to 20% by weight, preferentially ranging from 10% to 20% by weight and more preferentially ranging from 15% to 20% by weight, relative to the total weight of the composition.

In a known manner, all the compositions of the invention may contain one or more adjuvants that are common in cosmetics and dermatology, hydrophilic or lipophilic gelling agents and/or thickeners; moisturizers; emollients; hydrophilic or lipophilic active agents; free-radical scavengers; sequestering agents; antioxidants; preserving agents; acidifying or basifying agents; fragrances; film-forming agents; soluble dyes; and mixtures thereof. The amounts of these various adjuvants are those conventionally used in foundations.

As active agents that may be used in the composition of the invention, mention may be made, for example, of moisturizers, such as protein hydrolysates and polyols, for instance glycerol, glycols, for instance polyethylene glycols, and sugar derivatives; natural extracts; anti-inflammatories; procyannidolic oligomers; vitamins, for instance vitamin A (retinol), vitamin E (tocopherol), vitamin C (ascorbic acid), vitamin B5 (panthenol), vitamin B3 (niacinamide), derivatives of these vitamins (especially esters) and mixtures thereof; urea; caffeine; salicylic acid and its derivatives; α-hydroxy acids such as lactic acid and glycolic acid and derivatives thereof; retinoids such as carotenoids and vitamin A derivatives; sunscreens; hydrocortisone; melatonin; algal, fungal, plant, yeast or bacterial extracts; enzymes; steroids; antibacterial active agents, for instance 2,4,4'-trichloro-2'-hydroxydiphenyl ether (or triclosan), 3,4,4'-trichlorocarbanilide (or triclocarban) and the acids indicated above and especially salicylic acid and its derivatives; tensioning agents; and mixtures thereof.

Needless to say, a person skilled in the art will take care to select the optional adjuvant(s) added to the composition according to the invention such that the advantageous properties intrinsically associated with the composition in accordance with the invention are not, or are not substantially, adversely effected by the envisaged addition.

Advantageously, the composition according to the invention may have a viscosity, measured at 25° C., at a shear rate of 200 s$^{-1}$, ranging from 0.25 to 0.5 Pa·s (2.5 to 5 poises), and preferably ranging from 0.3 to 0.45 Pa·s (3 to 4.5 poises). Such a viscosity allows a satisfactorily sliding application of the composition on the skin. The viscosity is measured at 25° C. using a Rheomat RM 180 viscometer equipped with a no. 2 spindle, the measurement being performed after 10 minutes of rotating the spindle (after which time stabilization of the viscosity and of the spin speed of the spindle are observed), at a shear rate of 200 s$^{-1}$.

The invention is illustrated in greater detail in the example that follows.

EXAMPLE 1

A foundation in the form of a water-in-oil emulsion having the composition below was prepared:

| Oily phase: | |
|---|---|
| Isododecane | 13 g |
| Cyclopentasiloxane | 11.9 g |
| Cyclohexasiloxane | 7 g |
| Polydimethylsiloxane (DC 200 Fluid - 5 cst from the company Dow Corning) | 2.5 g |
| Isoeicosane | 2 g |
| Hexyl laurate | 0.6 g |
| Isostearyl neopentanoate | 0.5 g |
| Cetyl dimethicone copolyol (Abil ® EM 90 from the company Goldschmidt) | 0.8 g |
| Dimethicone copolyol (KF6017 from Shin Etsu) | 5 g |
| Polyglyceryl isostearate (4 mol of glycerol) | 0.6 g |
| Hectorite | 1.6 g |
| Iron oxides coated with perfluoroalkyl phosphate | 0.7 g |
| Titanium oxide coated with perfluoroalkyl phosphate | 11.2 g |
| Nacre | 2 g |
| Polymethyl methacrylate powder | 4 g |
| Aqueous phase | |
| Glycerol | 7 g |
| Butylene glycol | 3 g |
| Sodium chloride | 0.7 g |
| Preserving agents | |
| Water | qs 100 g |

The emulsion is prepared at room temperature, on the one hand by mixing the pigments in some of the cyclopentasiloxane, and on the other hand by mixing the other oils with the surfactants, after which the mixture of pigments and the polymethyl methacrylate powder are added to the other mixed constituents of the fatty phase. The mixture of the constituents of the aqueous phase is then prepared and is poured into the mixture of the fatty phase, with stirring according to the means known to obtain the final emulsion.

This foundation applies easily to the skin and gives a good sensation of creaminess and softness, and a very good sliding effect; it dries quickly after application of the product, and the makeup result obtained shows good uniformity of color, without leaving any marks on the skin.

The invention claimed is:

1. A fluid foundation composition in the form of a water-in-oil emulsion, comprising:
at least one volatile hydrocarbon-based oil in an amount ranging from 8% to 15% by weight relative to the total weight of the composition;
at least one first volatile silicone oil with a flash point of greater than or equal to 55° C. and less than or equal to 80° C. in an amount ranging from 8% to 16% by weight relative to the total weight of the composition;
at least one second volatile silicone oil with a flash point of greater than or equal to 80° C. and less than or equal to 95° C. in an amount ranging from 4% to 15% by weight relative to the total weight of the composition;
at least 8% by weight of dyestuff; and
an aqueous phase comprising:
water;
a first water miscible polyol comprising 3 carbon atoms and being present in an amount ranging from 5% to 8% by weight, relative to the total weight of the composition; and
a second water miscible polyol chosen from butylene glycol, pentylene glycol, hexylene glycol, dipropylene glycol, diethylene glycol, and mixtures thereof, in an amount ranging from 1% to 7% by weight, relative to the total weight of the composition,
wherein the water, the polyol, and the oil are present in an amount such that the weight ratio of (water+polyol) to oil is greater than or equal to 0.8.

2. The composition of claim 1, wherein the total content of the polyols is greater than or equal to 5% by weight relative to the total weight of the composition.

3. The composition of claim 1, wherein the aqueous phase further comprises poly methyl methacrylate particles,
wherein the water is the predominant component of the emulsion, and the composition has a viscosity ranging from 0.25 Pa·s to 0.6 Pa·s.

4. The composition of claim 1, wherein the at least one volatile hydrocarbon-based oil is chosen from hydrocarbon-based oils with a flash point ranging from 40° C. to 102° C.

5. The composition of claim 1, wherein the at least one volatile hydrocarbon-based oil is chosen from hydrocarbon-based oils with a flash point ranging from 40° C. to 50° C.

6. The composition of claim 1, wherein the at least one volatile hydrocarbon-based oil is chosen from volatile hydrocarbon-based oils containing from 8 to 16 carbon atoms, and mixtures thereof.

7. The composition of claim 1, wherein the at least one volatile hydrocarbon-based oil is chosen from branched C8-C16 alkanes, branched C8-C16 esters, and mixtures thereof.

8. The composition of claim 1, wherein the at least one volatile hydrocarbon-based oil is chosen from isododecane, isodecane and isohexadecane.

9. The composition of claim 8, wherein the at least one volatile hydrocarbon-based oil is isododecane.

10. The composition of claim 1, wherein the first and/or second volatile silicone oils are chosen from linear or cyclic silicone oils containing from 2 to 7 silicon atoms, wherein these silicones optionally comprise alkyl or alkoxy groups containing from 1 to 10 carbon atoms.

11. The composition of claim 10, wherein the first and/or second volatile silicone oils are chosen from octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane, and mixtures thereof.

12. The composition of claim 1, wherein at least one volatile silicone oil is present in the composition in an amount ranging from 5% to 35% by weight, relative to the total weight of the composition.

13. The composition of claim 1, wherein at least one volatile silicone oil is present in the composition in an amount ranging from 15% to 25% by weight, relative to the total weight of the composition.

14. The composition of claim 1, wherein the first volatile silicone oil has a flash point ranging from 67° C. to 85° C.

15. The composition of claim 1, wherein the first volatile silicone oil is chosen from decamethylcyclopentasiloxane and decamethyltetrasiloxane.

16. The composition of claim 8, wherein the second volatile silicone oil is dodecamethylcyclohexasiloxane.

17. The composition of claim 1, wherein the second volatile silicone oil has a flash point ranging from 87° C. to 95° C.

18. The composition of claim 1, comprising a mixture of decamethylcyclopentasiloxane, dodecamethylcyclohexasiloxane and isododecane.

19. The composition of claim 18, wherein, in the mixture, the content, expressed on a weight basis relative to the total weight of the composition, is such that: isododecane content>decamethylcyclopentasiloxane content>dodecamethylcyclohexasiloxane content.

20. The composition of claim 1, wherein the composition contains isodecane as the at least one volatile hydrocarbon-based oil in a predominant amount based on weight relative to the total weight of the composition.

21. The composition of claim 1, wherein the composition comprises decamethylcyclopentasiloxane in a predominant amount, based on weight relative to the content of any other volatile silicone oil that may be present in the composition.

22. The composition of claim 1, wherein the composition comprises at least one nonvolatile oil.

23. The composition of claim 22, wherein the at least one nonvolatile oil is chosen from nonvolatile hydrocarbon-based oils, nonvolatile silicone oils, and mixtures thereof.

24. The composition of claim 23, wherein the at least one nonvolatile oil is present in an amount ranging from 0.1% to 12% by weight, relative to the total weight of the composition.

25. The composition of claim 24, wherein the at least one nonvolatile oil is present in an amount ranging from 1% to 5% by weight, relative to the total weight of the composition.

26. The composition of claim 1, wherein the composition comprises oils present in an amount ranging from 30% to 45% by weight, relative to the total weight of the composition.

27. The composition of claim 26, wherein the composition comprises oils present in amount ranging from 30% to 40% by weight, relative to the total weight of the composition.

28. The composition of claim 1, wherein the composition comprises from 15% to 35% by weight of water, relative to the total weight of the composition.

29. The composition of claim 28, wherein the composition comprises from 22% to 28% by weight of water, relative to the total weight of the composition.

30. The composition of claim 1, wherein the first water miscible polyol is present in an amount greater than the total content of the second water miscible polyol.

31. The composition of claim 1, wherein the second polyol is present in the composition in an amount ranging from 2% to 4% by weight, relative to the total weight of the composition.

32. The composition of claim 1, wherein the aqueous phase is present in the composition in an amount ranging from 20% to 50% by weight, relative to the total weight of the composition.

33. The composition of claim 1, wherein the weight ratio of (water+polyol)/oil ranges from 0.8 to 1.2.

34. The composition of claim 33, wherein the weight ratio of (water+polyol)/oil ranges from 0.94 to 1.2.

35. The composition of claim 1, wherein the composition comprises a C8-C22 alkyl dimethicone copolyol.

36. The composition of claim 35, wherein the C8-C22 alkyl dimethicone copolyol is a compound of formula (I) below:

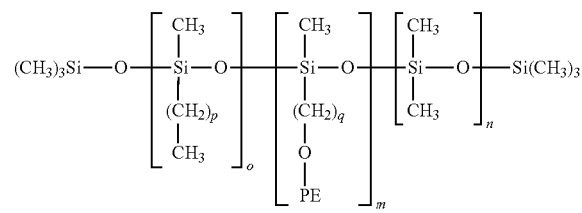

wherein:
PE represents (—C2H4O)$_x$-(C3H6O)$_y$-R, in which R is chosen from a hydrogen atom and an alkyl radical of 1 to 4 carbon atoms, x ranges from 0 to 100, y ranges from 0 to 80, x plus y cannot simultaneously be 0;
m ranges from 1 to 40;
n ranges from 10 to 200;
o ranges from 1 to 100;
p ranges from 7 to 21; and
q ranges 0 to 4.

37. The composition of claim 36, wherein:
R is H;
m ranges from 1 to 10;
n ranges from 10 to 100;
o ranges from 1 to 30;
p equals 15; and
q=3.

38. The composition of claim 33, wherein the C8-C22 alkyl dimethicone copolyol is cetyl dimethicone copolyol.

39. The composition of claim 1, wherein the composition comprises a dimethicone copolyol.

40. The composition of claim 39, wherein the dimethicone copolyol is a compound of formula (II) below:

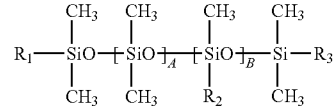

in which:
$R_1$, $R_2$ and $R_3$, independently of each other, are chosen from $C_1$-$C_6$ alkyl radicals, or a $R_3$ is not an alkyl radical;
$R_4$ is chosen from hydrogen, a $C_1$-$C_3$ alkyl radical or a $C_2$-$C_4$ acyl radical;
A and B are chosen from integers ranging from 0 to 200 and 0 to 50 respectively, with the proviso that A and B cannot both simultaneously equal 0;
x is an integer ranging from 1 to 6;
y is an integer ranging from 1 to 30; and
z is an integer ranging from 0 to 5.

41. The composition of claim 40, wherein $R_1$ and $R_3$ are methyl radicals, x is an integer ranging from 2 to 6, and y is an integer ranging from 4 to 30.

42. The composition of claim 41, wherein $R_4$ is hydrogen.

43. The composition of claim 39, wherein the dimethicone copolyol is a compound of formula (III) below:

$$(CH_3)_3SiO-[(CH_3)_2SiO]_A-(CH_3SiO)_B-Si(CH_3)_3$$
$$|$$
$$(CH_2)_2-(OCH_2CH_2)_y-OH$$
(III)

in which A is an integer ranging from 20 to 105, B is an integer ranging from 2 to 10 and Y is an integer ranging from 10 to 20.

44. The composition of claim 39, wherein the dimethicone copolyol is a compound of formula (IV) below:

$$HO-(CH_2CH_2O)_y-(CH_2)_3-[(CH_3)_2SiO]_{A'}-$$
$$-[(CH_3)_2Si]-(CH_2)_3-(OCH_2CH_2)_y-OH$$
(IV)

in which A' and y are integers ranging from 10 to 20.

45. The composition of claim 39, wherein the dimethicone copolyol is present in the composition in an amount ranging from 2% to 10% by weight, relative to the total weight of the composition.

46. The composition of claim 45, wherein the dimethicone copolyol is present in the composition in an amount ranging from 5% to 7% by weight, relative to the total weight of the composition.

47. The composition of claim 1, wherein the composition further comprises a dyestuff.

48. The composition of claim 47, wherein the dyestuff is a pulverulent dyestuff.

49. The composition of claim 47, wherein the dyestuff is chosen from pigments, nacres, and mixtures thereof.

50. The composition of claim 49, wherein the pigments are chosen from iron oxide pigments and titanium dioxide pigments.

51. The composition of claim 48, wherein the pulverulent dyestuff is a coated hydrophobe.

52. The composition of claim 47, wherein the dyestuff is present in the composition in an amount ranging from 0.5% to 20% by weight, relative to the total weight of the composition.

53. The composition of claim 52, wherein the dyestuff is present in the composition in an amount ranging from 5% to 20% by weight, relative to the total weight of the composition.

54. The composition of claim 48, wherein the pulverulent dyestuff is present in the composition in an amount ranging from 8% to 20% by weight, relative to the total weight of the composition.

55. The composition of claim 54, wherein the pulverulent dyestuff is present in the composition in an amount ranging from 8% to 15% by weight, relative to the total weight of the composition.

56. The composition of claim 1, wherein the composition further comprises poly methyl methacrylate particles.

57. The composition of claim 56, wherein the poly methyl methacrylate particles are present in the composition in an amount ranging from 1% to 10% by weight, relative to the total weight of the composition.

58. The composition of claim 56, wherein the poly methyl methacrylate particles are present in the composition in an amount ranging from 2% to 6% by weight, relative to the total weight of the composition.

59. The composition of claim 56, wherein the dyestuffs are pulverulent dyestuffs and said pulverulent dyestuffs and said poly methyl methacrylate particles, are present in amounts such that the weight ratio of pulverulent dyestuff to poly methyl methacrylate particle ranges from 2.5 to 3.5.

60. The composition of claim 59, wherein the weight ratio of pulverulent dyestuff to poly methyl methacrylate particle ranges from 3 to 3.5.

61. The composition of claim 56, wherein the composition further comprises an additional filler other than the poly methyl methacrylate particles.

62. The composition of claim 61, wherein the additional filler is present in the composition in an amount ranging from 0.1% to 5% by weight, relative to the total weight of the composition.

63. The composition of claim 62, wherein the additional filler is present in the composition in an amount ranging from 0.1% to 3% by weight, relative to the total weight of the composition.

64. The composition of claim 1, wherein the composition comprises a total content of solid particles of less than or equal to 20% by weight, relative to the total weight of the composition.

65. The composition of claim 64, wherein said solid particles are chosen from pulverulent dyestuffs, polymethylmethacrylate particles, and additional fillers.

66. The composition of claim 64, wherein the total content of pulverulent dyestuffs, poly methyl methacrylate particles, and additional fillers ranges from 15% to 20% by weight relative to the total weight of the composition.

67. The composition of claim 1, wherein the composition comprises an oil thickener.

68. The composition of claim 67, wherein the oil thickener is chosen from organomodified clays and hydrophobic fumed silica.

69. The composition of claim 67, wherein the oil thickener is present in the composition in an amount ranging from 0.1% to 5% by weight, relative to the total weight of the composition.

70. the composition of claim 69, wherein the oil thickener is present in the composition in an amount ranging from 0.4% to 3% by weight, relative to the total weight of the composition.

71. The composition of claim 1, further comprising at least one additive chosen from gelling agents; hydrophilic or lipophilic thickeners and moisturizers; emollients; hydrophilic or lipophilic active agents; free-radical scavengers; sequestering agents; antioxidants; preserving agents; acidifying or basifying agents; fragrances; film-forming agents; soluble dyes; and mixtures thereof.

72. The composition of claim 1, wherein the viscosity of the composition ranges from 0.25 to 0.5 Pa·s, when measured at 25° C. and at a shear rate of 200 s−1.

73. The composition of claim 72, wherein the viscosity of the composition ranges from 0.3 to 0.45 Pa·s, when measured at 25° C. and at a shear rate of 200 s−1.

74. A nontherapeutic cosmetic process for making up the skin, comprising:
  applying to the skin a foundation composition in the form of a water-in-oil emulsion, said foundation composition comprising:
  at least one volatile hydrocarbon-based oil in an amount ranging from 8% to 15% by weight, relative to the total weight of the composition;
  at least one first volatile silicone oil with a flash point of greater than or equal to 55° C. and less than or equal to 80° C., in an amount ranging from 8% to 16% by weight, relative to the total weight of the composition;
at least one second volatile silicone oil with a flash point of greater than or equal to 80° C. and less than or equal to 95° C., in an amount ranging from 4% to 15% by weight, relative to the total weight of the composition;
at least 8% by weight of dyestuff; and
an aqueous phase comprising:
  water;
  a first water miscible polyol comprising 3 carbon atoms and being present in an amount ranging from 5% to 8% by weight, relative to the total weight of the composition; and
  a second water miscible polyol chosen from butylene glycol, pentylene glycol, hexylene glycol, dipropylene glycol, diethylene glycol, and mixtures thereof, in an amount ranging from 1% to 7% by weight, relative to the total weight of the composition,
wherein the water, the polyol, and the oil are present in an amount such that the weight ratio of (water+polyol) to oil is greater than or equal to 0.8.

75. The nontherapeutic cosmetic process of claim 74, wherein the foundation composition is applied to obtain a uniform and/or mark-free makeup result on the skin.

76. The composition of claim 74, wherein the at least one volatile hydrocarbon-based oil is chosen from hydrocarbon-based oils with a flash point ranging from 40° C. to 102° C.

77. The composition of claim 74, wherein the at least one volatile hydrocarbon-based oil is chosen from volatile hydrocarbon-based oils containing from 8 to 16 carbon atoms, and mixtures thereof.

78. The composition of claim 74, wherein the at least one volatile hydrocarbon-based oil is isododecane.

* * * * *

UNITED STATES PATENT AND TRADEMARK OFFICE
CERTIFICATE OF CORRECTION

PATENT NO.       : 8,529,918 B2                                     Page 1 of 1
APPLICATION NO.  : 10/784909
DATED            : September 10, 2013
INVENTOR(S)      : Nadia Gardel et al.

It is certified that error appears in the above-identified patent and that said Letters Patent is hereby corrected as shown below:

On Title page item (54) and in the Specification, Col. 1, lines 1 and 2:
"WATER-IN OIL EMULSION FOUNDATION COMPRISING A POLYOL" should read
--WATER-IN-OIL EMULSION FOUNDATION COMPRISING A POLYOL--.

In the Claims

In column 15, line 22:
"in which A' and yare integers..." should read --in which A' and y are integers...--.

Signed and Sealed this
First Day of July, 2014

Michelle K. Lee
*Deputy Director of the United States Patent and Trademark Office*